US010391299B2

(12) United States Patent
Marshall

(10) Patent No.: US 10,391,299 B2
(45) Date of Patent: Aug. 27, 2019

(54) INTERVENTIONAL MEDICAL SYSTEMS FOR THERAPY DELIVERY IN EXTRACARDIOVASCULAR SPACES AND ASSOCIATED TOOLS AND METHODS

(71) Applicant: Medtronic, Inc., Minneapolis, MN (US)

(72) Inventor: Mark T. Marshall, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 322 days.

(21) Appl. No.: 15/473,843

(22) Filed: Mar. 30, 2017

(65) Prior Publication Data
US 2018/0280684 A1 Oct. 4, 2018

(51) Int. Cl.
*A61N 1/05* (2006.01)
*A61B 17/00* (2006.01)
*A61B 17/34* (2006.01)
*A61B 17/32* (2006.01)

(52) U.S. Cl.
CPC .......... *A61N 1/05* (2013.01); *A61B 17/00234* (2013.01); *A61B 17/3468* (2013.01); *A61N 1/0504* (2013.01); *A61B 2017/00243* (2013.01); *A61B 2017/00389* (2013.01); *A61B 2017/320056* (2013.01)

(58) Field of Classification Search
CPC ...... A61N 1/05; A61N 1/0504; A61N 1/0563; A61B 17/3468; A61B 2017/320056; A61B 17/3415; A61B 17/07207; A61B 17/072; A61B 17/10; A61B 17/128; A61B 17/1285; A61B 2017/00389; A61B 2017/00243

USPC .......................................................... 606/129
See application file for complete search history.

(56) References Cited

U.S. PATENT DOCUMENTS

| 4,154,247 | A | 5/1979 | O'Neill |
| 4,998,975 | A | 3/1991 | Cohen et al. |
| 5,105,826 | A | 4/1992 | Smits et al. |

(Continued)

FOREIGN PATENT DOCUMENTS

| EP | 1323451 A2 | 7/2003 | |
| WO | WO-2016206015 A1 | * 12/2016 | .......... A61B 17/1285 |

OTHER PUBLICATIONS

Medtronic, Inc. 6996T Tunneling Tool, Technical Manual, 2011, 12 pages.

(Continued)

*Primary Examiner* — Katherine M Shi
*Assistant Examiner* — Andrew P. Restaino

(57) ABSTRACT

A tool for inserting an elongate medical device into a body includes a track (e.g. defined by inner surfaces of a base wall and opposing sidewalls), and a deployment assembly for moving the device along the track. A retainer of the assembly, fitted in sliding engagement within the track and limited to move only along a portion of the track, grips a first portion of a proximal length of the device; a slider of the assembly, also fitted in sliding engagement within the track and detachably joined to the retainer, receives a second portion of the device proximal length. When detached from the retainer, the slider is free to move along a distal length of the device, and can be moved along a distal segment of the track to disengage therefrom by separating from a distal terminal end of the guide.

17 Claims, 10 Drawing Sheets

(56) References Cited

U.S. PATENT DOCUMENTS

| | | |
|---|---|---|
| 5,388,578 A | 2/1995 | Yomtov et al. |
| 5,531,779 A | 7/1996 | Dahl et al. |
| 5,667,514 A | 9/1997 | Heller |
| 5,772,590 A | 6/1998 | Webster, Jr. |
| 7,047,086 B2 | 5/2006 | Taskiran et al. |
| 7,349,742 B2 | 3/2008 | Heil et al. |
| 7,890,191 B2 | 2/2011 | Rutten et al. |
| 7,899,555 B2 | 3/2011 | Morgan et al. |
| 8,050,773 B2 | 11/2011 | Zhu |
| 2014/0276928 A1 | 9/2014 | Vanderpool et al. |
| 2014/0324043 A1 | 10/2014 | Terwey et al. |
| 2014/0330208 A1 | 11/2014 | Christie et al. |
| 2014/0330248 A1 | 11/2014 | Thompson-Nauman et al. |
| 2014/0330287 A1 | 11/2014 | Thompson-Nauman et al. |
| 2014/0330325 A1 | 11/2014 | Thompson-Nauman et al. |
| 2014/0330326 A1 | 11/2014 | Thompson-Nauman et al. |
| 2014/0330327 A1 | 11/2014 | Thompson-Nauman et al. |
| 2014/0330328 A1 | 11/2014 | Thompson-Nauman et al. |
| 2014/0330329 A1 | 11/2014 | Thompson-Nauman et al. |
| 2014/0330331 A1 | 11/2014 | Thompson-Nauman et al. |
| 2015/0133951 A1 | 5/2015 | Seifert et al. |
| 2015/0133952 A1* | 5/2015 | Seifert ............... A61N 1/0504 606/129 |
| 2015/0306375 A1 | 10/2015 | Marshall et al. |
| 2015/0306410 A1 | 10/2015 | Marshall et al. |
| 2015/0342627 A1 | 12/2015 | Thompson-Nauman et al. |
| 2015/0343176 A1 | 12/2015 | Asleson et al. |
| 2016/0121106 A1 | 5/2016 | Marshall et al. |
| 2016/0121130 A1 | 5/2016 | Cinbis et al. |
| 2016/0157890 A1 | 6/2016 | Drake et al. |
| 2016/0158529 A1 | 6/2016 | Thompson-Nauman |
| 2016/0158530 A1 | 6/2016 | Drake et al. |
| 2016/0158567 A1 | 6/2016 | Marshall et al. |
| 2016/0175008 A1 | 6/2016 | Seifert et al. |
| 2016/0175580 A1 | 6/2016 | Marshall et al. |
| 2016/0175584 A1 | 6/2016 | Drake et al. |
| 2016/0235973 A1 | 8/2016 | Asleson et al. |
| 2017/0007287 A1 | 1/2017 | Malewicz et al. |
| 2017/0007297 A1 | 1/2017 | Drake et al. |
| 2017/0056115 A1 | 3/2017 | Corndorf et al. |

OTHER PUBLICATIONS (PCT/US2018/024257) PCT Notification of Transmittal of the International Search Report and the Written Opinion of the International Searching Authority, dated Jul. 2, 2018, 11 pages.

* cited by examiner

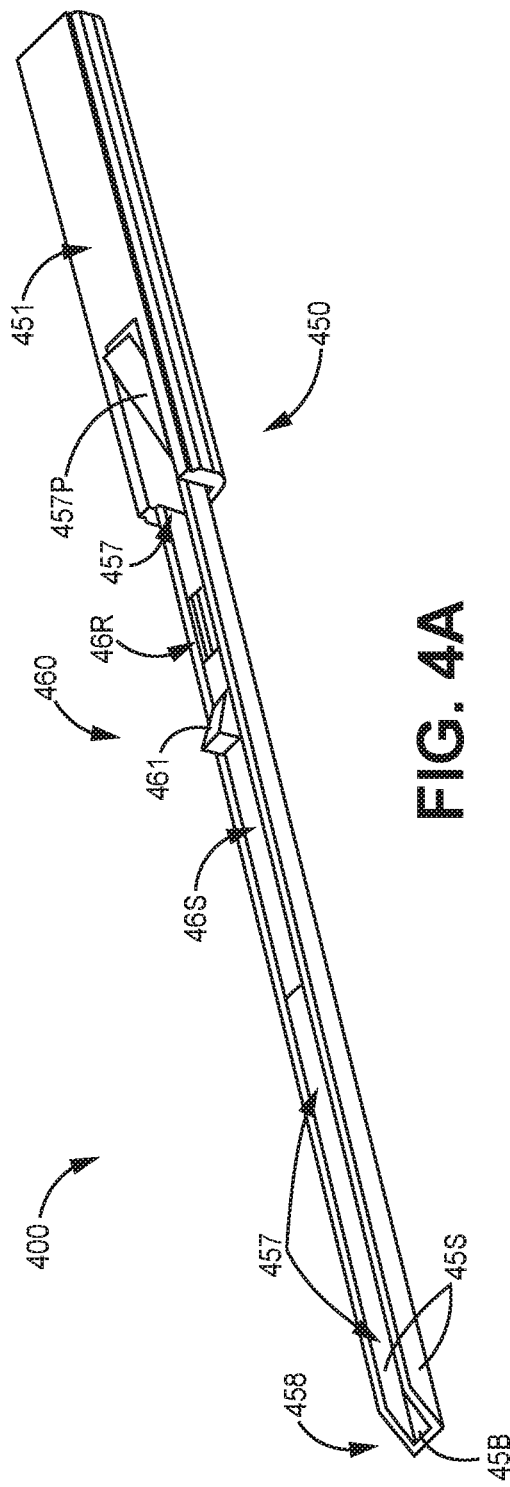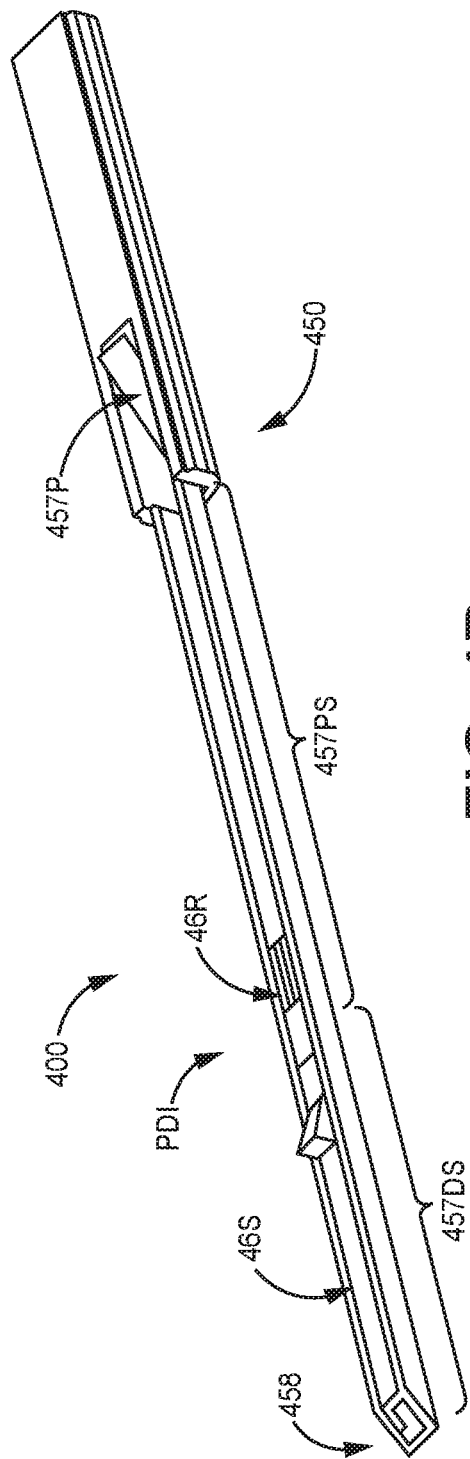

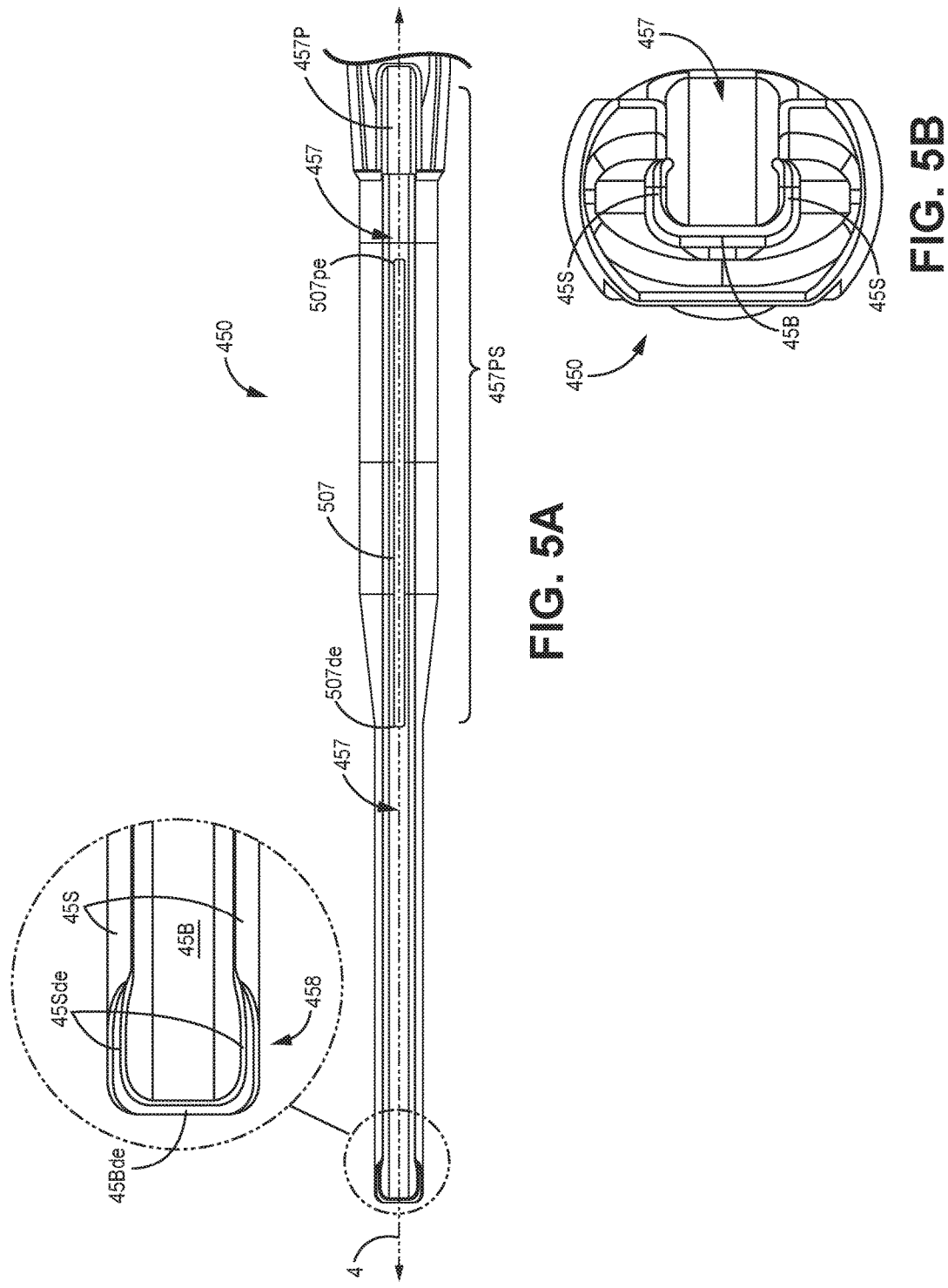

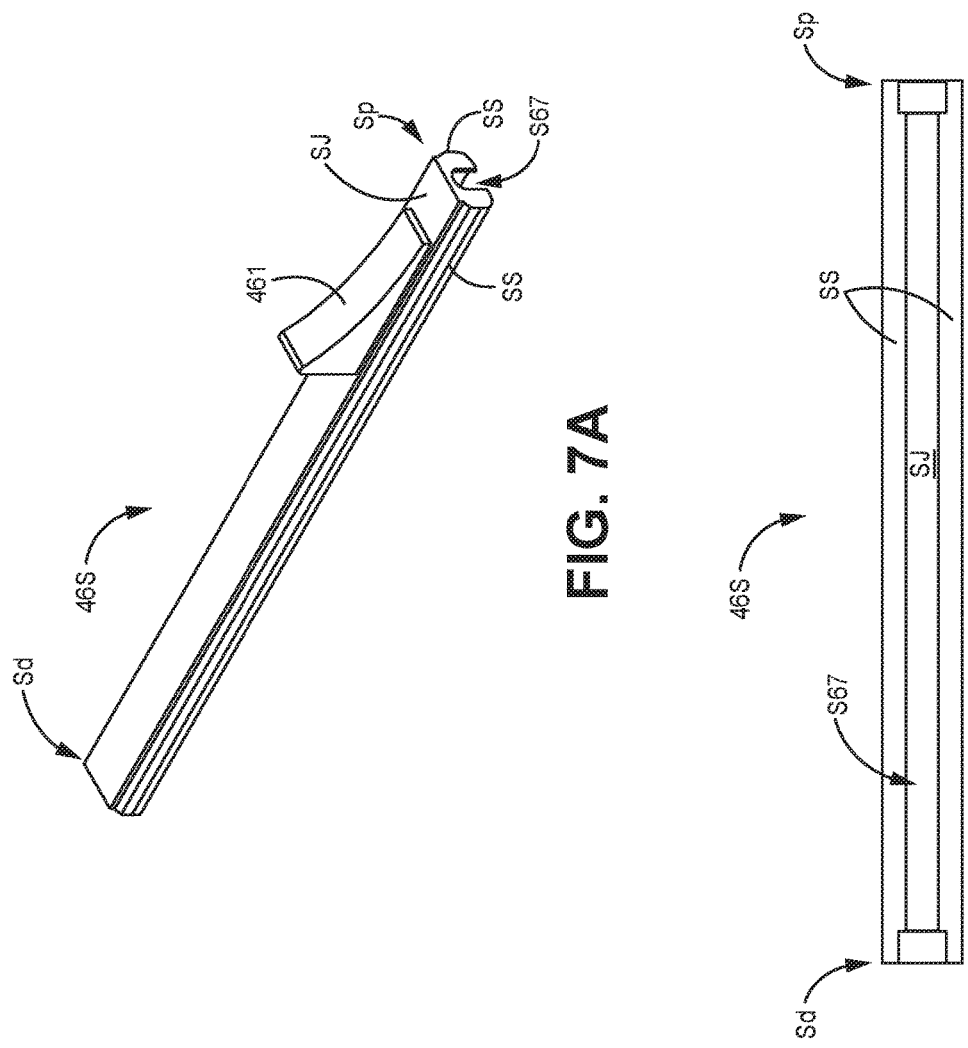
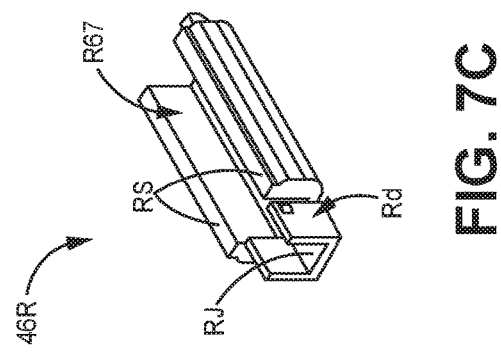

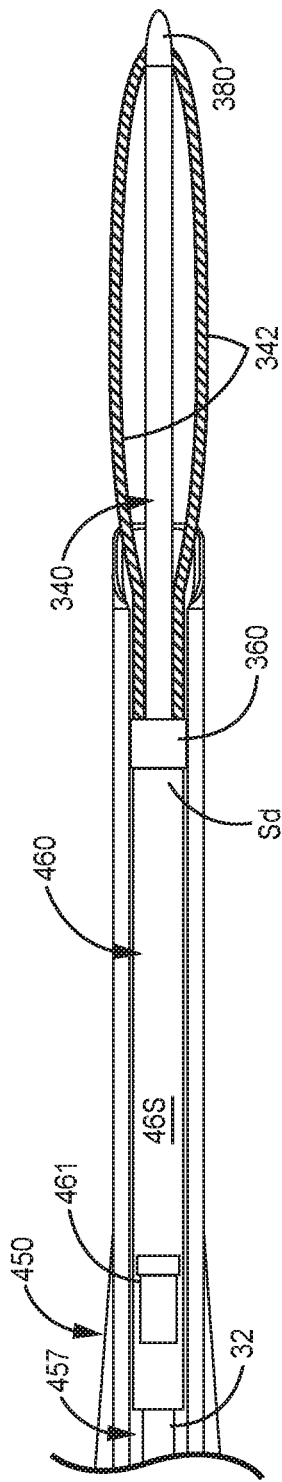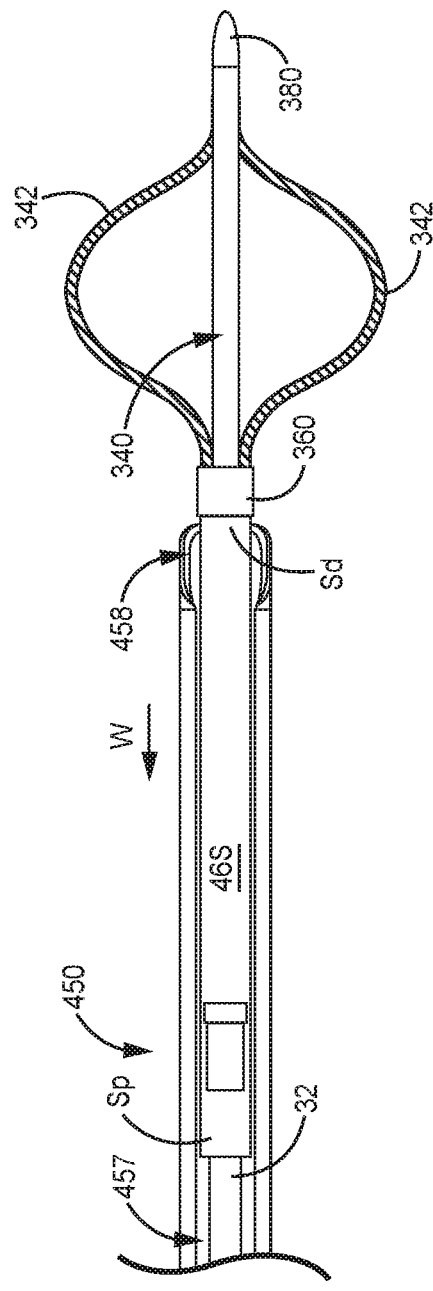

INTERVENTIONAL MEDICAL SYSTEMS FOR THERAPY DELIVERY IN EXTRACARDIOVASCULAR SPACES AND ASSOCIATED TOOLS AND METHODS

TECHNICAL FIELD

The present disclosure pertains to interventional medicine, and more particularly to systems and associated tools and methods for medical therapy delivery in extracardiovascular spaces.

BACKGROUND

Implantable medical electrical leads, included in systems that are known in the art for delivering cardiac therapy and/or for providing cardiac monitoring, are often implanted transvenously within a heart of a patient. But extracardiovascular implant sites may be preferred, for example, in those patients where vascular access is difficult, or because transvenous leads can become fibrosed in the heart over time, which makes lead revision and extraction procedures challenging.

SUMMARY

Disclosed herein are various embodiments of a tool for inserting an elongate medical device into a body of a patient, for example, for implant t at an extracardiovascular site such as one located in a substernal space. The tool includes a guide having a track formed therein, and a deployment assembly engaged with the track to move the elongate device, for example, an implantable medical electrical lead, along the track. The track may be defined by inner surfaces of a base wall and opposing sidewalls of the guide. According to some embodiments, a retainer of the deployment assembly is fitted in sliding engagement within the track, being limited to move only along a portion of the track, and being configured to grip a first portion of a proximal length of the device; a slider of the deployment assembly, which is detachably joined to the retainer, is also fitted in sliding engagement within the track, being configured to receive a second portion of the device proximal length that extends distally from the first portion. When the slider is detached from the retainer, the slider is free to move relative to the received device, along a distal length thereof, and along an entirety of a distal segment of the track, which extends between the track proximal segment and a distal terminal end of the guide. According to some embodiments and methods, the detached slider can be moved along the distal length of the track until the slider disengages therefrom and separates from the distal terminal end of the guide.

The retainer of the above-described deployment assembly may include a pair of opposing sidewalls and a joining wall that each have an inner surface defining an open channel of the retainer, wherein the retainer open channel is configured to receive and grip the device therein, and wherein, when the retainer is fitted within the above-described track, the inner surface of the retainer joining wall faces away from the inner surface of the guide base wall. The slider of the above-described deployment assembly may also include a pair of opposing sidewalls and joining wall that each have an inner surface defining an open channel of the slider; but, when the slider is joined to the retainer and fitted within the above-described track, the inner surface of the slider joining wall faces toward the inner surface of the guide base wall.

BRIEF DESCRIPTION OF THE DRAWINGS

The following drawings are illustrative of particular exemplary embodiments and do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIGS. 4A-B are perspective views of a tool, according to some embodiments, in which a deployment assembly thereof is shown in a first position and a second position, respectively;

FIG. 5A is a plan view of a portion of a guide of the tool, according to some embodiments, and includes an enlarged detail view;

FIG. 5B is an end view of the guide, according to some embodiments;

FIG. 7A is a perspective view of a slider of the deployment assembly, according to some embodiments;

FIG. 7B is a plan view of the slider, according to some embodiments;

FIG. 7C is a perspective view of a retainer of the deployment assembly, according to some embodiments;

FIG. 10A is a plan view of the system after the tool deployment assembly has been moved to insert the device into the body, according to some embodiments and methods; and FIG. 10B is a plan view of the system after the slider of the tool deployment assembly has moved along the device, according to some embodiments and methods.

DETAILED DESCRIPTION

The following detailed description is exemplary in nature and is not intended to limit, in any way, the scope, applicability, or configuration of the tools and techniques described in this disclosure. Rather, the following description provides practical examples, and those skilled in the art will recognize that some of the examples may have suitable alternatives.

Figure 1:
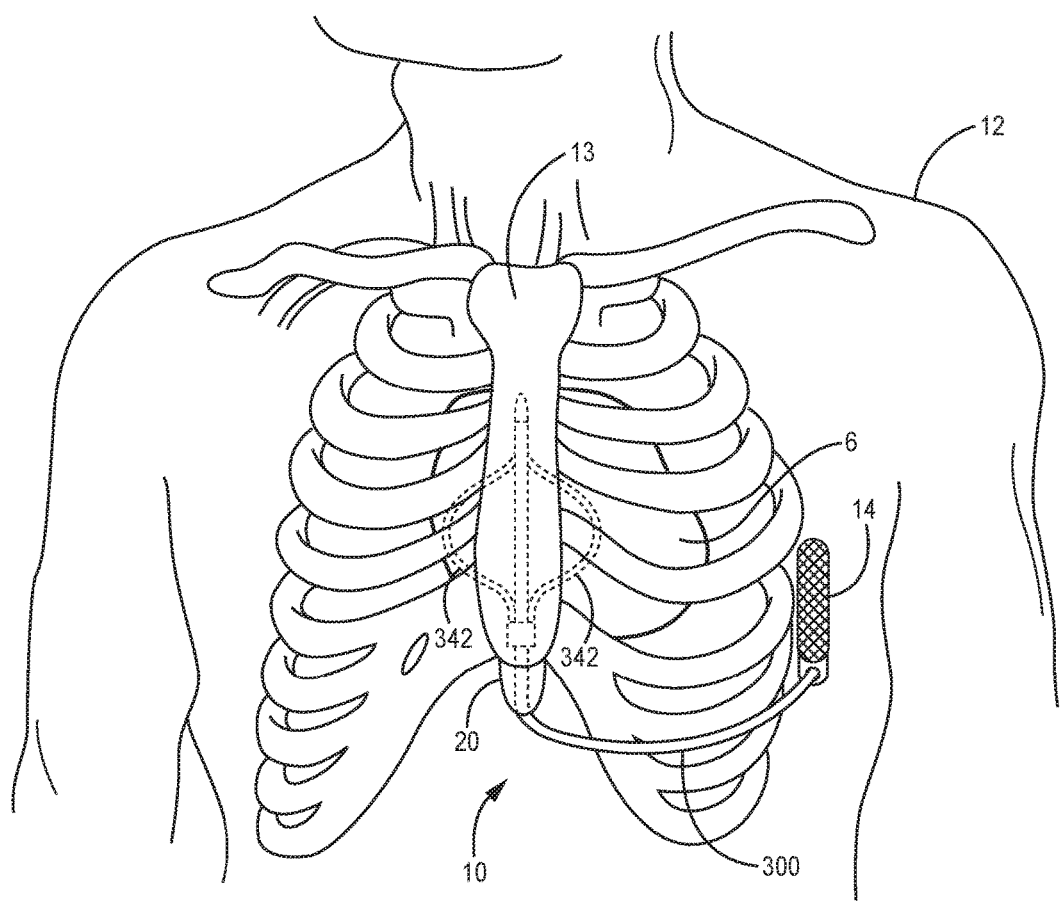
FIG. 1 is schematic showing an exemplary extracardiovascular implant.

FIG. 1 is a schematic showing an exemplary extracardiovascular implant of an exemplary system 10 that includes a pulse generator 14 coupled to an implantable medical electrical lead 300. Pulse generator 14 is shown implanted subcutaneously on the left mid-axillary of a patient 12, superficially of the patient's ribcage. Pulse generator 14, which may be configured to provide cardiac pacing and/or defibrillation therapy via lead 300, includes a hermetically sealed housing in which the appropriate electronics and a power supply are contained, and which is formed from a conductive material, such as titanium, or from a combination of conductive and non-conductive materials. Pulse generator 14 further includes a connector module by which lead 300 is electrically coupled to the electronics contained therein, for example, by electrical contacts contained within the connector module and a corresponding hermetically sealed feedthrough assembly, such as is known in the art. The conductive material of device housing may be employed as an electrode, for example, to provide the aforementioned therapy in conjunction with one or more pace/sense electrodes (shown in FIG. 3) and/or one or more defibrillation electrodes 342 of lead 300, which is shown implanted in a sub-sternal space, for example, within the loose connective tissue and/or sub-sternal musculature of the anterior mediastinum.

Figure 2:
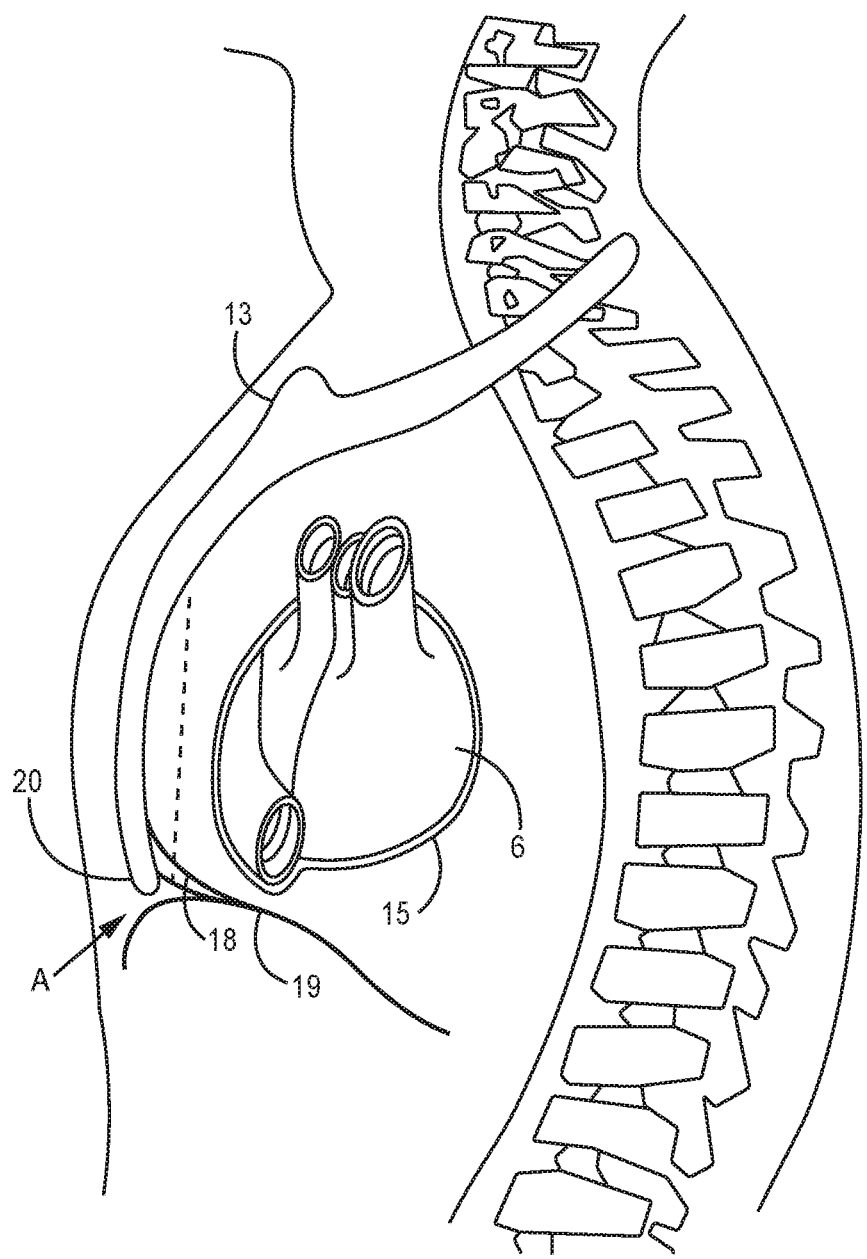
FIG. 2 is a schematic for describing sub-sternal access.

With reference to FIG. 2, the sub-sternal space may be defined as being bounded laterally by pleurae that enclose the patient's lungs (not shown), posteriorly by the pericardial sac 15 that encloses the patient's heart 6, and anteriorly by the sternum 13. In some instances, the anterior wall of the anterior mediastinum may also be formed by the transversus thoracics and one or more costal cartilages. FIG. 2 is a schematic showing an access site A for making a passageway between a patient's diaphragm 19 and xiphoid process 20 of sternum 13, for example, to create a sub-sternal tunnel (per the dashed line) in which to position a distal portion of a medical device, such as medical electrical lead 300. After making a superficial incision, an operator may open a passageway between diaphragmatic attachments 18 and diaphragm 19, for example, by blunt dissection. Tools and associated methods disclosed herein are configured to help an operator insert a distal portion of an elongate medical device into a patient's body, for example, directly into the substernal space of the anterior mediastinum region, without having to form a tunnel ahead of insertion of the device into the space. Thus, the inserted portion of the device fits snugly in the tissue, and the chance of introducing excess air into the space is mitigated. In other instances, the tools and associated methods disclosed herein may be utilized to insert at least a part of the distal portion of the elongate medical device within the pericardial space with the remainder of the distal portion inserted within the anterior mediastinum.

Figure 3:
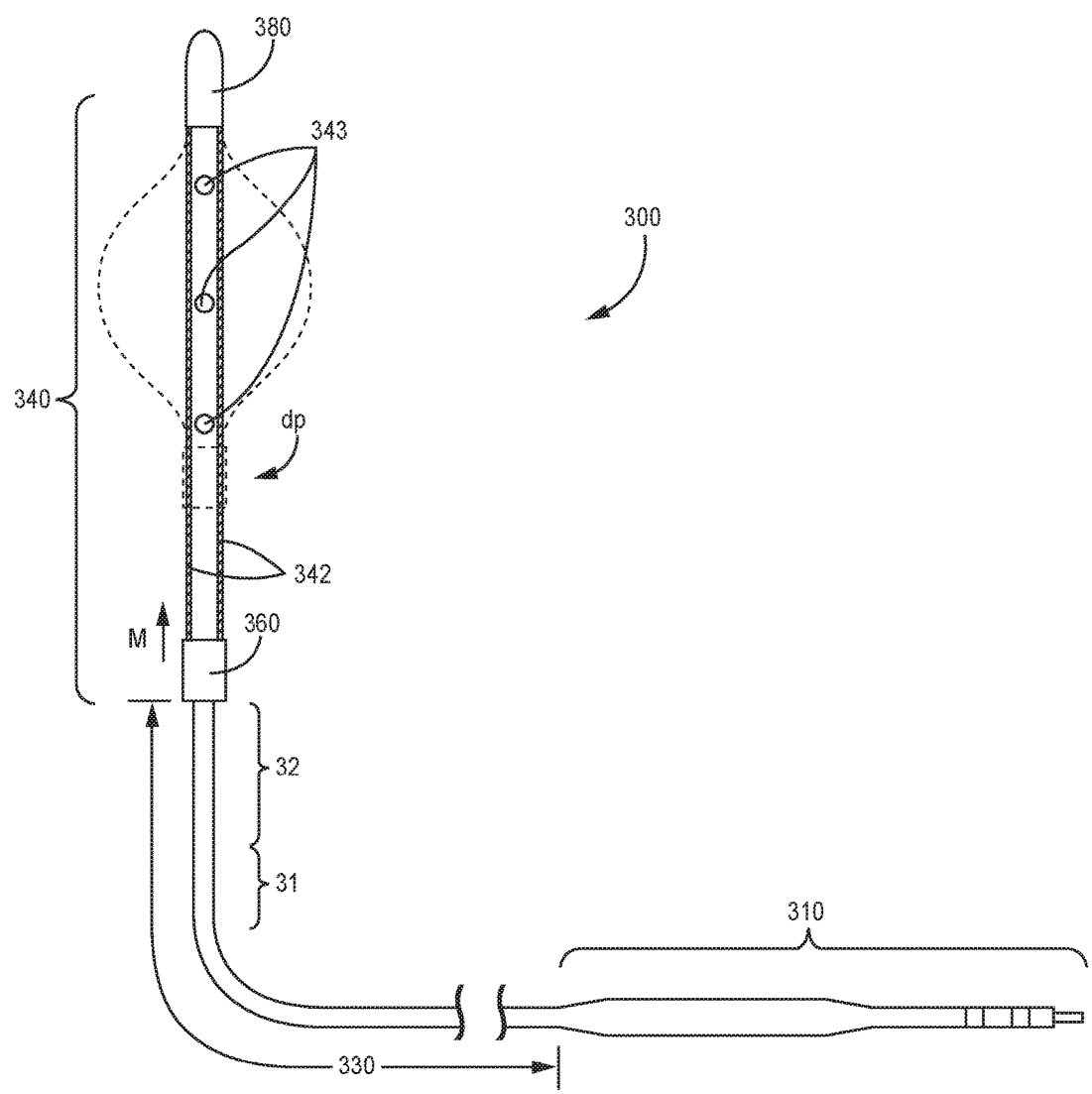
FIG. 3 is a plan view of an exemplary elongate medical device.

FIG. 3 is a plan view of an exemplary elongate medical lead 300, in the form of an implantable medical electrical lead compatible with tool embodiments described below. FIG. 3 illustrates lead 300 including electrodes 342, 343 and a connector terminal 310, for example, configured for electrically coupling electrodes 342, 343 to the above-described pulse generator 14 via the connector module. FIG. 3 further illustrates lead 300 including a proximal length 330, extending distally from connector terminal 310, a distal length 340, extending distally from proximal length 330, and a distal-most tip 380 terminating distal length 340. Although not shown, those skilled in the art of implantable medical electrical leads will appreciate that insulated conductor wires extend within lengths 330, 340 of lead 300 to couple each electrode 342, 343 to a corresponding contact of connector terminal 310.

According to some embodiments, a portion of device distal length 340, for example, that to which electrodes 343 are mounted, and distal-most tip 380 are relatively rigid. In one example, being formed from an implantable medical grade polymer such as a polyurethane. The polyurethane may, for instance, have a durometer of about 55 on the Shore D scale, but other relatively rigid polymers may also be utilized. Thus, as will be described in greater detail below, at least device distal length 340 may be pushed directly into a body of a patient, for example, within the substernal space, without having to first create a tunnel therein for the implant of electrodes 342, 343.

According to the illustrated embodiment, distal ends of electrodes 342 are secured to device distal length 340, within distal-most tip 380, or in close proximity thereto, and are coupled to one or more of the conductor wires, while proximal ends of electrodes 342 are secured to a collar 360 of lead 300, which is mounted in sliding engagement around distal length 340. With further reference to FIG. 3, electrodes 342 are deformable so that, when collar 360 is moved, per arrow M, from a proximal position to a distal position dp (collar 360 is illustrated with dashed lines at distal position dp), electrodes 342 bend in arcs according to the dashed line representation. Further detail concerning the construction of lead 300 may be found in the co-pending and commonly assigned U.S. patent application Ser. No. 14/973,818 published as U.S. 2016/0175580, which is hereby incorporated by reference in its entirety. However, the scope of the present invention is not limited by the particular configuration of exemplary lead 300.

Figure 6:
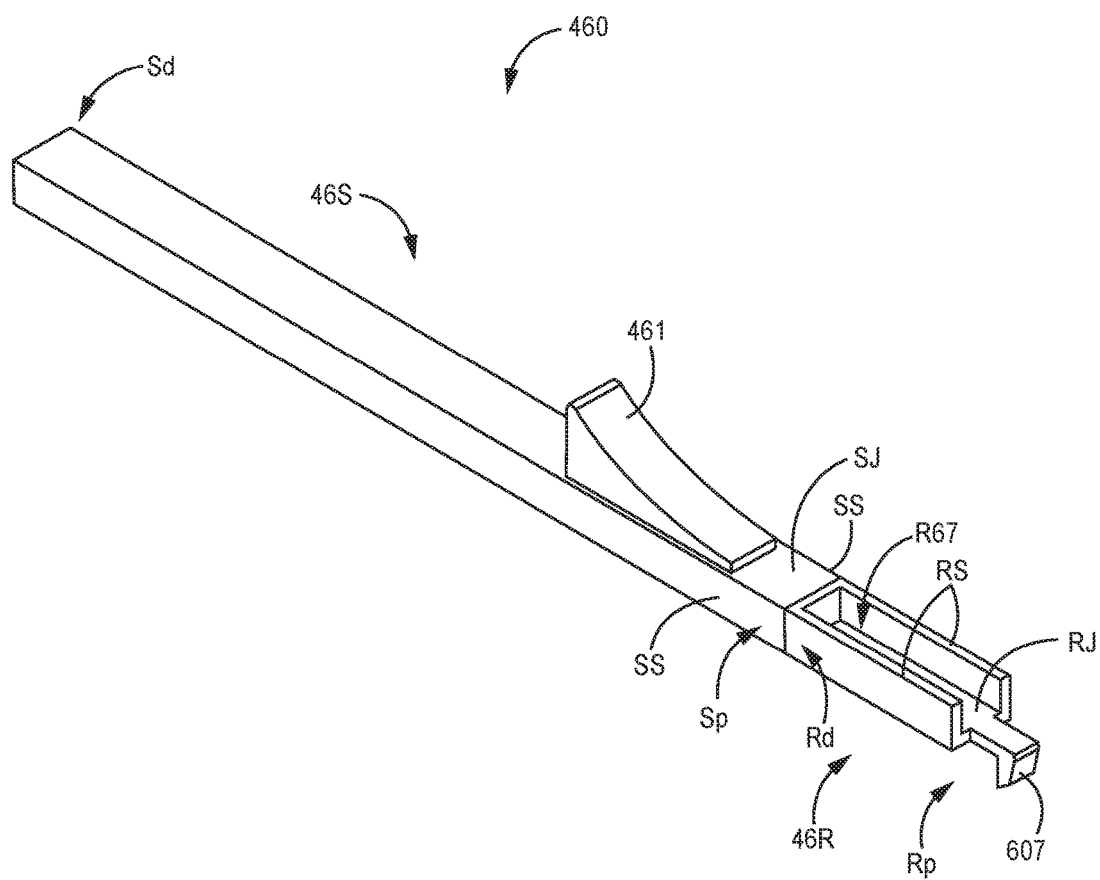
FIG. 6 is a perspective view of the deployment assembly of the tool separated from the guide, according to some embodiments.

FIGS. 4A-B are perspective views of a tool 400 for inserting an elongate medical device, such as lead 300, into a body of a patient, wherein FIG. 4A shows a deployment assembly 460 of tool 400 in a first position, and FIG. 4B shows deployment assembly 460 in a second position. FIGS. 4A-B further illustrate a handle 451 and a guide 450 that includes a distal terminal end 458, a proximal end 457P, and an elongate track 457 extending distally from proximal end 457P to distal terminal end 458. Guide 450 is joined to handle 451 at proximal end 457P. Deployment assembly 460 is shown including a retainer 46R and a slider 46S, which are each fitted in sliding engagement within guide track 457. With reference to FIGS. 5A-B, which are plan and end views of guide 450, track 457 is formed from a pair of opposing sidewalls 45S and a base wall 45B. Base wall 45B extends between sidewalls 45S so that inner surfaces thereof define track 457. FIG. 6 is a perspective view of deployment assembly 460 separated from track 457, wherein retainer 46R and slider 46S are detachably joined together. FIG. 6 illustrates retainer 46R including a pair of opposing sidewalls RS and a joining wall RJ that extends therebetween so that inner surfaces thereof define an open channel R67 of retainer 46R, which extends from a proximal end Rp to a distal end Rd of retainer 46R. FIG. 6, and the perspective and plan views of FIG. 7A-B illustrate slider 46S including a pair of opposing sidewalls SS and a joining wall SJ that extends therebetween such that inner surfaces thereof define an open channel S67, which extends from a proximal end Sp to a distal end Sd of slider 46S. According to the illustrated embodiment, when retainer 46R and slider 46S are joined together, retainer open channel R67 is continuous with slider open channel S67, and both open channels R67, S67 are configured to receive lead 300 therein, with a portion of retainer open channel R67 at retainer distal end Rd configured to grip lead 300, so that deployment assembly 460 can move lead 300 along guide track 457, as described in greater detail below. In FIG. 7C, a perspective view of retainer 46R, the gripping portion of channel R67 at distal end Rd can be seen.

With further reference to FIGS. 4A-B, and 6, deployment assembly retainer 46R is fitted in guide track 457 such that the inner surface of retainer joining wall RJ faces away from the inner surface of track base wall 45B, whereas deployment assembly slider 46S is fitted in guide track 457 such that the inner surface of slider joining wall SJ faces toward the inner surface of track base wall 45B. According to some embodiments, slider 46S and retainer 46R are detachably joined together by overlapping sidewalls SS at slider proximal end Sp onto sidewalls RS at retainer distal end Rd. FIG.

7C shows retainer sidewalls RS having a thinner cross-section at distal end Rd for the purpose of such an overlapping junction, which may be held together by a press-fit and/or snap fit, according to some embodiments. In FIG. 4A, at the aforementioned first position of deployment assembly 460, slider 46S and retainer 46R are joined together and an operator can move assembly 460 along track 457 and toward the second position of FIG. 4B by applying a push force to slider 46S, for example, with a thumb or finger engaged with a control feature 461 formed in an outer surface of slider joining wall SJ. With reference to FIG. 4B, guide track 457 may be divided into a proximal segment 457PS and a distal segment 457DS, wherein, at an intersection of the proximal and distal segments PDI, a stop feature may be located and configured to engage with a projecting member of retainer 46R. Thus, as illustrated in FIG. 4B, when the projecting member of retainer 46R engages with the stop feature of track 457, the operator may detach slider 46S from retainer 46R and continue to move slider distally toward distal terminal end 458 of guide 450.

With reference to FIG. 5A, according to some embodiments, base wall 45B of guide 450 has a slot 507 formed therethrough, which extends only along proximal segment 457PS, so that the aforementioned stop feature of guide track 457 is formed by a distal-most edge 507*de* of slot 507. According to the illustrated embodiment, and with reference to FIG. 6, the aforementioned projecting member of retainer 46R is formed by a fin 607 that extends from an outer surface of retainer joining wall RJ and engages with slot 507 when retainer 46R is fitted in guide track 457. FIG. 5A further illustrates a proximal-most edge 507*pe* of slot 507 being offset from track proximal end 457P, for example, to prevent deployment assembly 460 from pinching an elongate device loaded therein against handle 451.

Figure 8:
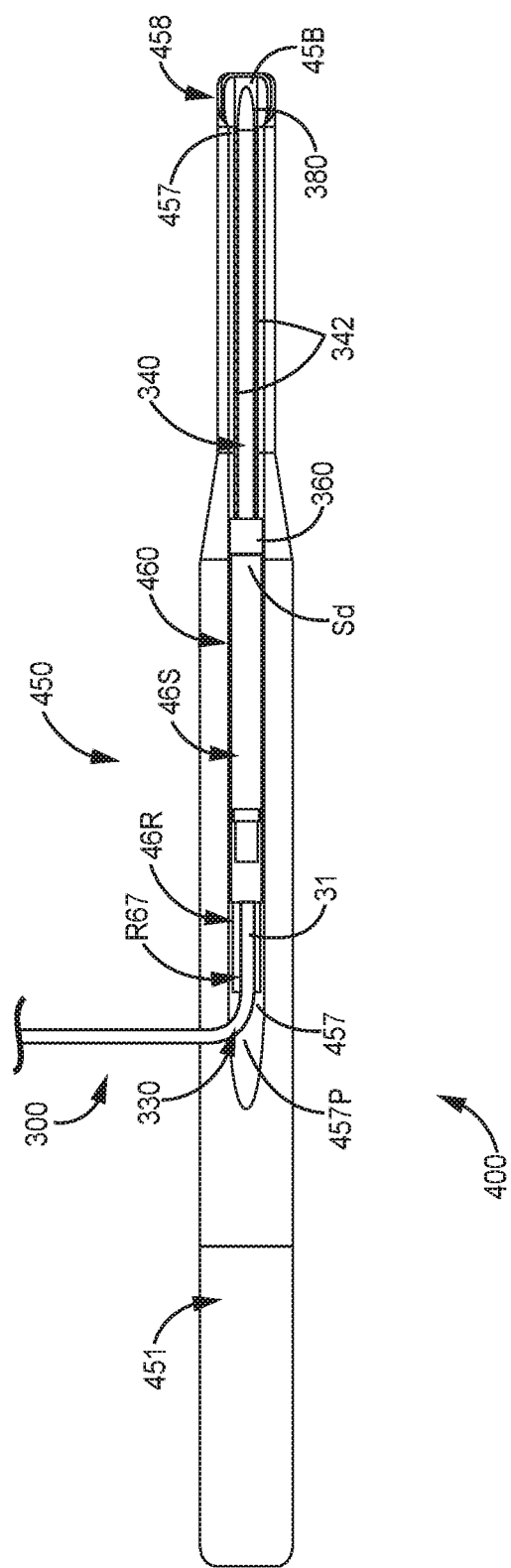
FIG. 8 is a plan view of the exemplary device loaded in the tool, according to some embodiments of a system.

FIG. 8 is a plan view of exemplary lead 300 loaded in tool 400, according to some embodiments of a system, wherein guide track 457 of tool 400 receives lead 300 in sliding engagement therein. FIG. 8 illustrates device distal length 340 received in guide track 457, such that device distal-most tip 380 is located in close proximity to guide distal terminal end 458, and distal end Sd of deployment assembly slider 46S confronts device collar 360 in the proximal position where deformable electrodes 342 extend in a generally straight line to fit within track 457 alongside device distal length 340. With reference to FIG. 3 in conjunction with FIG. 8, device proximal length 330 may be positioned in track 457 such that a first portion 31 thereof extends in open channel R67 of deployment assembly retainer 46R, and open channel S67 of deployment assembly slider 46S (FIGS. 7A-B) extends around a second portion 32 of device proximal length 330. According to some embodiments, proximal end 457P of guide track 457 is formed in a ramp, which may be best seen in FIGS. 4A-B, so that device proximal length 330 is 'gently' guided out from track 457. According to some methods, the operator can load lead 300 into tool deployment assembly 460, either before or after deployment assembly 460 is fitted into guide track 457, by pressing first portion 31 of device proximal length 330 into the grip of retainer open channel R67 prior to attaching slider 46S to retainer 46R. With reference back to FIG. 5A, the enlarged detail of guide distal terminal end 458 shows distal terminal edges 45Sde of sidewalls 45S recessed from a distal terminal edge 45Sde of base wall 45B, according to some embodiments, which may facilitate a fitting of deployment assembly 460 into guide track 457.

According to an exemplary embodiment of tool 400, an overall length of deployment assembly 460, when slider 46S and retainer 46R are attached, may be about 3.5 to 4 inches; an overall length of guide track 457 may be about 8 to 8.5 inches; an overall length of slot 507 about 4 inches; and an overall length of slider 46S about 3 inches. Guide 450 may be molded from a relatively rigid medical grade plastic, such as a Polyether ether ketone (PEEK) or an acetyl resin; and deployment assembly slider 46S and retainer 46R may each be molded from a relatively rigid medical grade polyurethane, for example, having a durometer of about 55 on a shore D scale.

Figure 9:
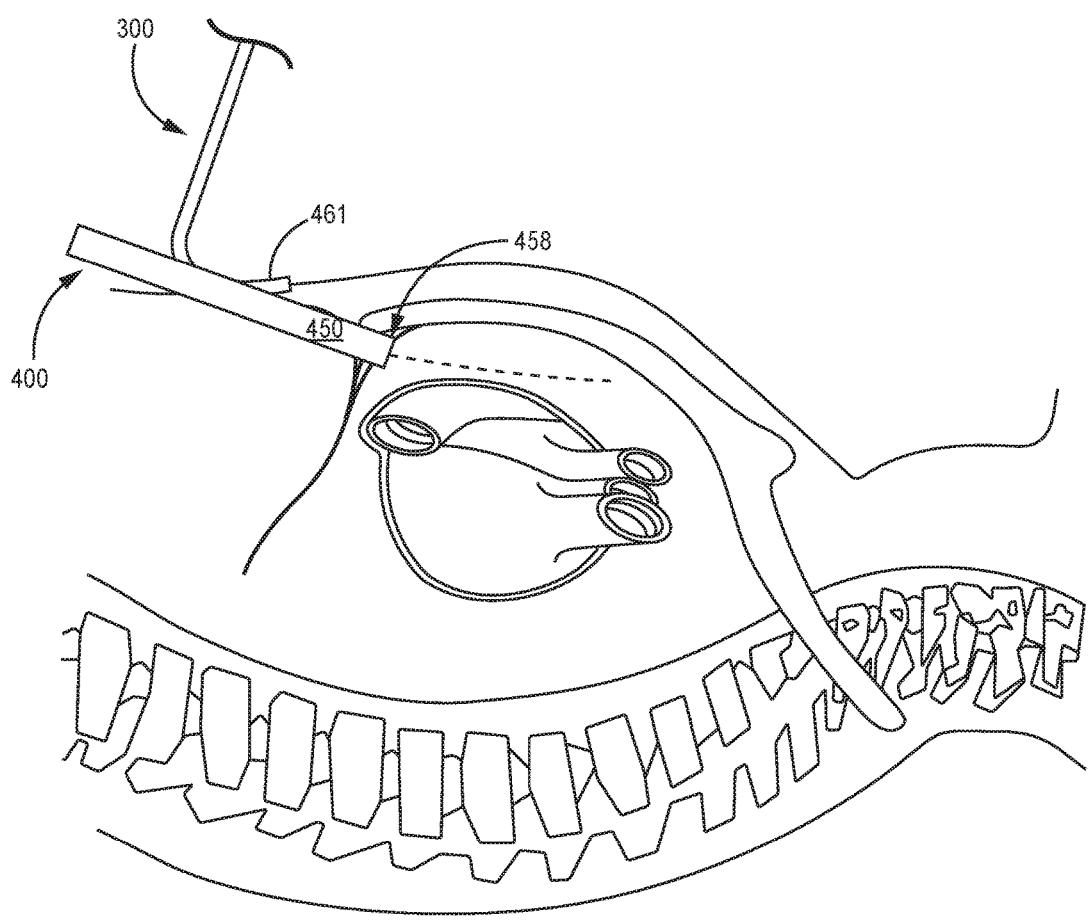
FIG. 9 is a schematic showing the system positioned for inserting the device into a body of a patient, according to some methods.

FIG. 9 shows the system of FIG. 8 positioned for inserting lead 300 into a body of a patient, according to some methods. With reference back to FIG. 2 and the associated description, the operator may open a passageway between diaphragmatic attachments 18 and diaphragm 19, for example, by blunt dissection, and then position distal terminal end 458 of tool guide 450 within the opening, as shown. FIG. 9 illustrates tool guide 450 oriented such that deployment assembly control feature 461 faces away from the patient's body for the operator to engage and push lead 300 into the substernal space, for example, along the dashed line. Distal length 340 of lead 300, or a distal length of any other elongate device loaded into tool 400, is relatively rigid and terminated by a tapered, yet blunt distal-most tip, such as tip 380 described above, so that the distal length of the device will, in response to the push force applied to deployment assembly 460, advance into the substernal space without buckling. Thus, the operator may move deployment assembly 460 distally along track 457, for example, from the first position of FIG. 4A, and toward the second position of FIG. 4B, to advance lead 300 along track 457 and into the substernal space, so that device distal-most tip 380 creates a tunnel that provides a 'snug' fit for device distal length 340. With reference back to FIG. 8, lead 300 is oriented in tool guide 450 with electrodes 343 (FIG. 3) facing toward base wall 45B of track 457, so that when lead 300 is advanced into the substernal space electrodes 343 will face toward the patient's heart 6. In some instances, sidewalls 45S may include channels (not shown) that receive electrodes 342 to ensure appropriate orientation of lead 300 within track 457.

As described above, in conjunction with FIG. 4B, track 457 may include a stop feature configured to engage with a projecting member of retainer 46R, when the operator has moved deployment assembly 460 to the second position and device distal length 340 is inserted into the patient's body. The stop curtails further distal movement of deployment assembly 460 along track 457 and designates a point at which the operator may detach deployment assembly slider 46S from deployment assembly retainer 46R, as shown in FIG. 4B, so that slider 46S may be moved distally, independent of retainer 46R, along track 457 and device distal length 340, with first portion 31 of device proximal length 330 still being gripped by retainer 46R. FIGS. 10A-B are plan views of the system after slider 46S has been detached from retainer 46R and moved distally along lead 300 so that second portion 32 of device proximal length 330 is exposed. FIG. 10A illustrates the confronting engagement of slider distal end Sd with device collar 360 starting to move collar 360 distally along device distal length 340 to deform deformable electrodes 342; and FIG. 10B illustrates slider 46S having moved collar 360 out from track 457 so that each of deformable electrodes 342 bends in an arc. After collar 360 has been moved out from track 457, first portion 31 of device proximal length 330 may be lifted out from the grip of retainer 46S and guide 450 may be separated from lead 300 and the detached slider 46S by withdrawing guide 450, per arrow W, relative to detached slider 46S, until proximal end Sp of slider 46S separates from distal terminal end 458 of guide 450.

In the foregoing detailed description, various tool features have been described with reference to specific embodiments. However, it may be appreciated that various modifications and changes can be made without departing from the scope of the invention as set forth in the appended claims. For example, one or more features of a particular exemplary embodiment may be employed by other exemplary embodiments in the same or alternative forms.

The invention claimed is:

1. A tool for inserting an elongate medical device into a body of a patient, the tool comprising:
 a handle;
 a guide including:
  a proximal end coupled to the handle,
  a distal terminal end, and
  an elongate track extending along a longitudinal axis of the tool from the proximal end to the distal terminal end of the guide, the track being formed from a base wall and a pair of opposing sidewalls of the guide, the base wall extending between the sidewalls such that inner surfaces thereof define the track, the track including a track proximal segment extending distally from the proximal end of the guide, a track distal segment extending from the track proximal segment to the distal terminal end of the guide, and a stop feature located at an intersection of the track proximal segment and the track distal segment; and
 a deployment assembly configured to receive the device therein and to move the device along the track of the guide, the deployment assembly comprising:
  a retainer including:
   a proximal end;
   a distal end;
   a pair of opposing sidewalls,
   a joining wall extending between the retainer sidewalls such that inner surfaces of the retainer sidewalls and the retainer joining wall define an open channel that extends from the retainer proximal end to the retainer distal end, the open channel being configured to receive and grip the device therein, the retainer fitting in sliding engagement within the track of the guide such that the inner surface of the joining wall faces away from the inner surface of the guide base wall, and
   a projecting member configured to engage with the stop feature of the track; and
  a slider detachably joined to the retainer, the slider including:
   a proximal end;
   a distal end;
   a pair of opposing sidewalls; and
   a joining wall extending between the slider sidewalls such that inner surfaces thereof define an open channel of the slider that extends from the slider proximal end to the slider distal end, the slider open channel being sized to receive the device therein and being continuous with the retainer open channel, the slider fitting in sliding engagement within the track of the guide such that the inner surface of the slider joining wall faces toward the track.

2. The tool of claim 1, wherein:
 the base wall of the guide has a slot formed therethrough, the slot extending only along the proximal segment of the track, and the stop feature of the track comprising a distal-most edge of the slot; and
 the projecting member of the retainer comprises a fin that extends from an outer surface of the retainer joining wall, the fin being engaged in the slot when the retainer is fitted within the track.

3. The tool of claim 2, wherein the slot of the guide track is offset distally from the proximal end of the track.

4. The tool of claim 1, wherein a distal-most edge of each of the opposing sidewalls of the guide is recessed from a distal-most edge of the base wall of the guide at the distal terminal end of the guide.

5. The tool of claim 1, wherein the proximal end of the guide track comprises a ramp.

6. The tool of claim 1, wherein the deployment assembly slider further includes a control feature formed on the outer surface of the slider joining wall, the control feature being configured for engagement with a thumb or finger of an operator.

7. The tool of claim 1, wherein the sidewalls of the deployment assembly slider at the proximal end thereof overlap the sidewalls of deployment assembly retainer at the distal end thereof to detachably join the slider to the retainer.

8. A system for delivering medical therapy, the system comprising:
 an elongate medical device comprising:
  a proximal length,
  a distal length extending distally from the proximal length,
  a distal-most tip terminating the distal length; and
 a tool for inserting the elongate medical device into a body of a patient, the tool comprising:
  a handle;
  a guide including:
   a proximal end joined to the handle;
   a distal terminal end, and
   an elongate track extending from the proximal end to the distal terminal end and along a longitudinal axis of the tool, the track being formed from a base wall and a pair of opposing sidewalls of the guide, the base wall extending between the sidewalls such that inner surfaces thereof define the track, the track receiving the device in sliding engagement therein, and the track including a proximal segment extending distally from the proximal end, a distal segment extending from the track proximal segment to the distal terminal end of the guide, and a stop feature located at an intersection of the proximal and distal segments; and
  a deployment assembly configured to receive first and second portions of the device proximal length therein, and to move the device along the track of the guide, the second portion extending between the first portion and the device distal length, and the deployment assembly comprising:
   a retainer extending from a proximal end thereof to a distal end thereof, the retainer including a pair of opposing sidewalls, a joining wall, and a projecting member, the retainer opposing sidewalls and joining wall forming an open channel of the retainer that extends from the retainer proximal end to the retainer distal end, the joining wall extending between the retainer sidewalls such that inner surfaces thereof define the open channel, the open channel receiving and gripping the first portion of the device proximal length therein, the retainer fitting in sliding engagement within the track of the guide such that the inner surface of the joining wall faces away from the inner surface of the guide base wall and the fin engages in the slot of the track, and the projecting member projecting being configured to engage with the stop feature of the track, when the retainer is fitted therein; and a slider extending from a proximal end thereof to a distal end thereof, the slider being detachably joined to the retainer, the slider including a pair of opposing sidewalls and a joining wall forming an open channel of the slider that extends from the slider proximal end to the slider distal end, the slider joining wall extending between the slider sidewalls such that inner surfaces thereof define the slider open channel, the slider open channel receiving the second portion of the device proximal length therein, the slider open channel being continuous with the retainer open channel, and the slider fitting in sliding engagement within the track of the guide such that the inner surface of the slider joining wall faces toward the inner surface of the guide base wall.

9. The system of claim 8, wherein the distal length of the device includes a relatively rigid segment; and the distal-most tip of the device is tapered.

10. The system of claim 8, wherein:
the device further comprises a collar and an elongate deformable electrode extending from a proximal end thereof to a distal end thereof, the proximal end of the deformable electrode being secured to the collar, the distal end of the deformable electrode being secured to the device distal length, in proximity to the distal-most tip of the device, and the collar being mounted in sliding engagement around the device distal length; and the distal end of the tool deployment assembly slider confronts the device collar, when the device proximal length is received in the deployment assembly, to move the collar along the device distal length from a proximal position to a distal position, when the slider is detached from the tool deployment assembly retainer, the proximal position being that at which the deformable electrode extends in a generally straight line alongside the device distal length and in close proximity thereto, and the distal position being that at which the deformable electrode bends in an arc.

11. The system of claim 10, wherein:
the distal length of the device includes a relatively rigid segment;
the device further comprises another electrode mounted to the rigid segment; and
the distal-most tip of the device is tapered.

12. The system of claim 8, wherein:
the base wall of the tool guide has a slot formed therethrough, the slot extending only along the proximal segment of the guide track, and the stop feature of the track comprising a distal-most edge of the slot; and
the projecting member of the tool retainer comprises a fin that extends from an outer surface of the retainer joining wall, the fin being engaged in the slot of the guide track when the retainer is fitted within the track.

13. The system of claim 12, wherein the slot of the tool guide track is offset distally from the proximal end of the track.

14. The system of claim 8, wherein a distal-most edge of each of the opposing sidewalls of the tool guide is recessed from a distal-most edge of the base wall of the guide at the distal terminal end of the guide.

15. The system of claim 8, wherein the proximal end of the track of the tool guide comprises a ramp.

16. The system of claim 8, wherein the tool deployment assembly slider further includes a control feature formed on the outer surface of the slider joining wall, the control feature being configured for engagement with a thumb or finger of an operator.

17. The system of claim 8, wherein the sidewalls of the tool deployment assembly slider at the proximal end thereof overlap the sidewalls of tool deployment assembly retainer at the distal end thereof to detachably join the slider to the retainer.

* * * * *